US010772620B2

(12) United States Patent
Sauer et al.

(10) Patent No.: US 10,772,620 B2
(45) Date of Patent: Sep. 15, 2020

(54) ADJUSTABLE MOTION LIMITER FOR A MINIMALLY INVASIVE SURGICAL DEVICE

(71) Applicant: LSI Solutions, Inc., Victor, NY (US)

(72) Inventors: Jude S. Sauer, Pittsford, NY (US); John F. Hammond, Canandaigua, NY (US)

(73) Assignee: LSI Solutions, Inc., Victor, NY (US)

( * ) Notice: Subject to any disclaimer, the term of this patent is extended or adjusted under 35 U.S.C. 154(b) by 130 days.

(21) Appl. No.: 15/243,163

(22) Filed: Aug. 22, 2016

(65) Prior Publication Data

US 2017/0049441 A1 Feb. 23, 2017

Related U.S. Application Data

(60) Provisional application No. 62/207,880, filed on Aug. 20, 2015.

(51) Int. Cl.
*A61B 17/04* (2006.01)
*A61B 17/06* (2006.01)
*A61B 90/00* (2016.01)

(52) U.S. Cl.
CPC ........... *A61B 17/0469* (2013.01); *A61B 2017/06042* (2013.01); *A61B 2090/034* (2016.02)

(58) Field of Classification Search
CPC .......... A61B 17/0469; A61B 2090/034; A61B 2017/06042; A61B 2017/00367; A61B 2017/0042; A61B 2017/2841; A61B 2017/2845; A61B 2017/2909; A61B 2017/2913; A61B 2017/2915; A61B 2017/2946; A61B 17/2841; A61B 17/2845; A61B 2017/048; A61B 2017/291–2925; A61B 2017/047–0477; A61B 17/29; A61B 17/2909
(Continued)

(56) References Cited

U.S. PATENT DOCUMENTS 3,682,175 A * 8/1972 Halter .................. A61D 7/00
604/184
4,164,225 A 8/1979 Johnson
(Continued)

OTHER PUBLICATIONS 0000-00-00 Product Literature; , , LSI Solutions® Sew-Right SR.5™, The Single Squeeze Suturing Device™.
(Continued)

*Primary Examiner* — Katrina M Stransky
*Assistant Examiner* — Brigid K Byrd
(74) *Attorney, Agent, or Firm* — David J. Gervasi; Christopher B. Miller (57) ABSTRACT

An adjustable motion limiter for a minimally invasive surgical device is disclosed. The adjustable motion limiter includes a cam surface and a positioning interface. Another adjustable motion limiter for a minimally invasive surgical device is disclosed. The adjustable motion limiter has a positioning interface comprising a grooved protrusion. The adjustable motion limiter also has a cam surface comprising an arcuate surface and facing a direction which is substantially perpendicular to a direction the positioning interface faces. The adjustable motion limiter further has an adjustment key and one or more locking teeth. A minimally invasive surgical device having an adjustable motion limiter is also disclosed.

18 Claims, 9 Drawing Sheets

(58) Field of Classification Search
USPC .......................................... 606/144; 30/233
See application file for complete search history.

(56) References Cited

U.S. PATENT DOCUMENTS

| | | | |
|---|---|---|---|
| 4,406,654 A * | 9/1983 | Bristow | A61D 7/00 604/209 |
| 4,546,859 A * | 10/1985 | Newman | A61M 5/31555 188/67 |
| 4,865,029 A * | 9/1989 | Pankratov | A61B 18/20 606/4 |
| 4,887,756 A * | 12/1989 | Puchy | A61B 17/0644 227/142 |
| 5,282,806 A * | 2/1994 | Haber | A61B 17/29 606/139 |
| 5,364,365 A * | 11/1994 | Wortrich | A61B 17/3496 604/158 |
| 5,431,666 A | 7/1995 | Sauer | |
| 5,562,686 A | 10/1996 | Sauer | |
| 5,582,615 A * | 12/1996 | Foshee | A61B 17/2909 606/139 |
| 5,766,183 A * | 6/1998 | Sauer | A61B 17/0469 606/139 |
| 6,368,334 B1 | 4/2002 | Sauer | |
| 6,533,796 B1 | 3/2003 | Sauer | |
| 6,997,931 B2 | 2/2006 | Sauer | |
| 7,211,093 B2 | 5/2007 | Sauer | |
| 7,407,505 B2 | 8/2008 | Sauer | |
| 7,731,727 B2 | 6/2010 | Sauer | |
| 8,313,496 B2 | 11/2012 | Sauer | |
| 8,398,657 B2 | 3/2013 | Sauer | |
| 8,652,149 B2 | 2/2014 | Sauer | |
| 8,827,136 B2 * | 9/2014 | Hessler | A61B 17/0469 227/175.2 |
| 9,433,431 B2 | 9/2016 | Aue | |
| 2002/0095175 A1 * | 7/2002 | Brock | A61B 34/20 606/205 |
| 2002/0107530 A1 | 8/2002 | Sauer | |
| 2004/0059358 A1 * | 3/2004 | Kortenbach | A61B 17/0643 606/153 |
| 2004/0068272 A1 | 4/2004 | Sauer | |
| 2005/0165419 A1 | 7/2005 | Sauer | |
| 2005/0234479 A1 | 10/2005 | Hatch | |
| 2007/0255296 A1 | 11/2007 | Sauer | |
| 2009/0222027 A1 | 9/2009 | Sauer | |
| 2010/0211083 A1 | 8/2010 | Sauer | |
| 2011/0087218 A1 * | 4/2011 | Boudreaux | A61B 18/1445 606/41 |
| 2011/0087255 A1 * | 4/2011 | McCormack | A61B 5/04005 606/167 |
| 2011/0118758 A1 | 5/2011 | Sauer | |
| 2012/0016383 A1 | 1/2012 | Sauer | |

OTHER PUBLICATIONS 0000-00-00 Product Literature; , , LSI Solutions® RD Technology Guide.

0000-00-00 Product Literature; , , LSI Solutions® RD Running Device™ Surgery's Best Suturing Technology™.

0000-00-00 Product Literature; , , LSI Solutions® Sew-Right SR.5™ Device and SR.5™ Quick Load™ Inservice Guide.

Jun. 16, 2010 Symposium; Knight, Peter , For Presentation at the STS 2011 Annual Meeting—Automated Remote Transapical Wound Closure System: Fresh Porcine Heart Bursting Pressure Study and Cadaver Endoscopic Demonstration.

Jun. 21, 2010 Symposium; Leigh, H. , For Presentation at the STS 2011 Annual Meeting—Fresh Porcine Heart Bursting Pressure Study Fig. 1.

Sep. 1, 2017, International Preliminary Report on Patentability; Woo, Julian W.

International Search Report dated Jan. 19, 2017 for PCT Application: PCT/US2016/048020.

* cited by examiner

ADJUSTABLE MOTION LIMITER FOR A MINIMALLY INVASIVE SURGICAL DEVICE

RELATED APPLICATION

This patent application claims priority to U.S. Provisional Patent Application No. 62/207,880 filed Aug. 20, 2015 and entitled "ADJUSTABLE MOTION LIMITER FOR A MINIMALLY INVASIVE SURGICAL DEVICE". The 62/207,880 application is hereby incorporated by reference in its entirety.

FIELD

The claimed invention relates to minimally invasive surgical devices, and more specifically to an adjustable motion limiter for minimally invasive surgical devices having an actuator.

BACKGROUND

Figure 1:
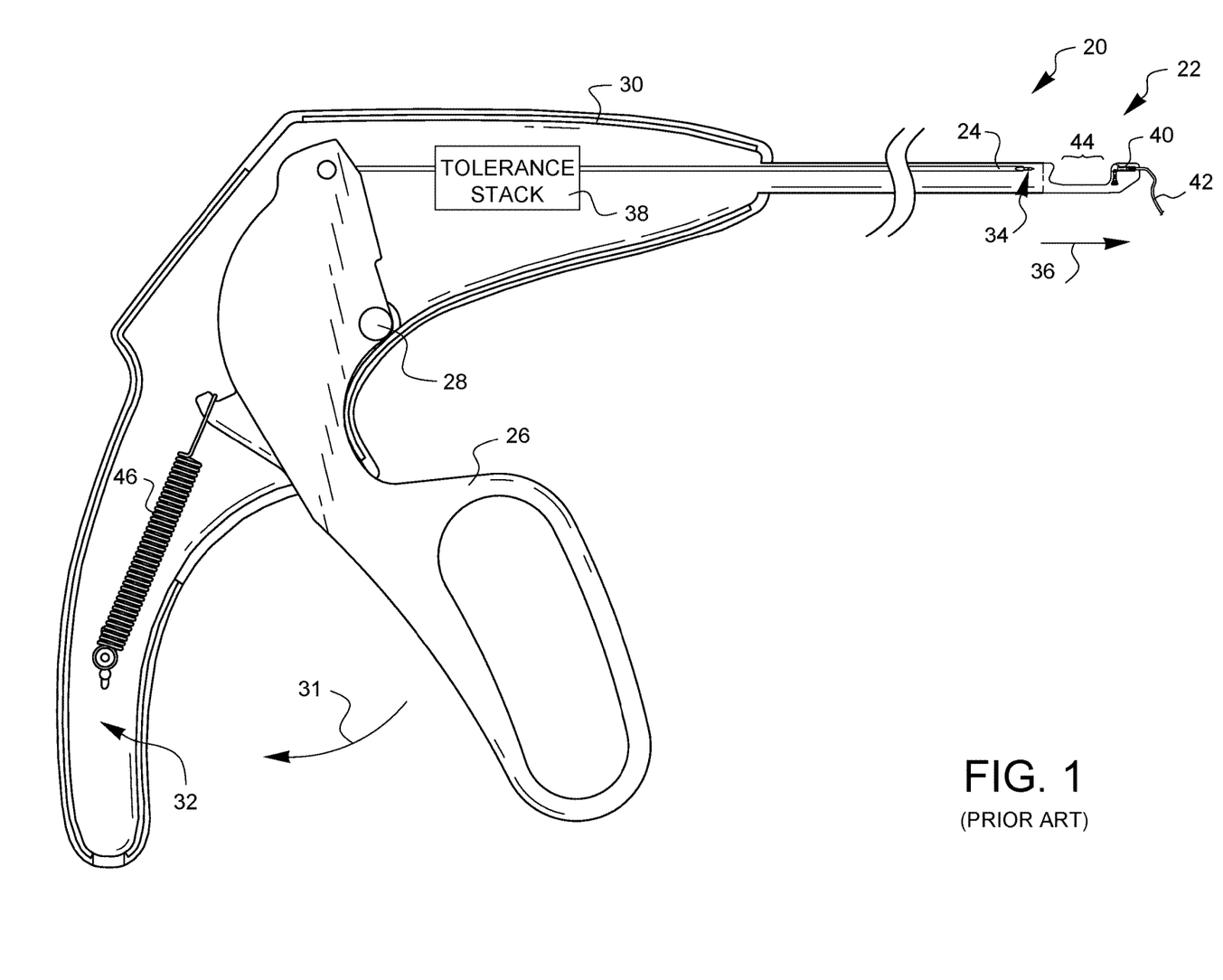
FIG. 1. illustrates one embodiment of a minimally invasive surgical device.

FIG. 1. illustrates one embodiment of a minimally invasive surgical device 20. This particular device 20 is a suturing device having an end effector 22 that includes a needle 24. The needle 24 is coupled to an actuator 26, in this example, a handle which pivots on a pivot point 28 in the housing 30. When the actuator 26 is squeezed in the direction of arrow 31 a handle 32 which is part of the housing 30, a needle tip 34 of the needle 24 will move in a distal direction 36. A tolerance stack 38 is schematically illustrated to account for the fact that there are many different tolerances which can cause the amount of distance which the needle tip 34 moves to vary. The suturing device 20 is equipped with a ferrule 40 which lies at the end of a suture 42. Ideally, the actuator 26 moves the needle tip 34 across the tissue bite area 44 and into contact with the ferrule 40, such that the ferrule 40 is engaged by interference contact with the needle tip 34 without undesired deformation of the ferrule 40. The actuator 26 can then be returned to its starting position by spring 46, causing the needle 24 to draw the ferrule 40 and its suture 42 back through the tissue bite area 44.

Figure 2A:
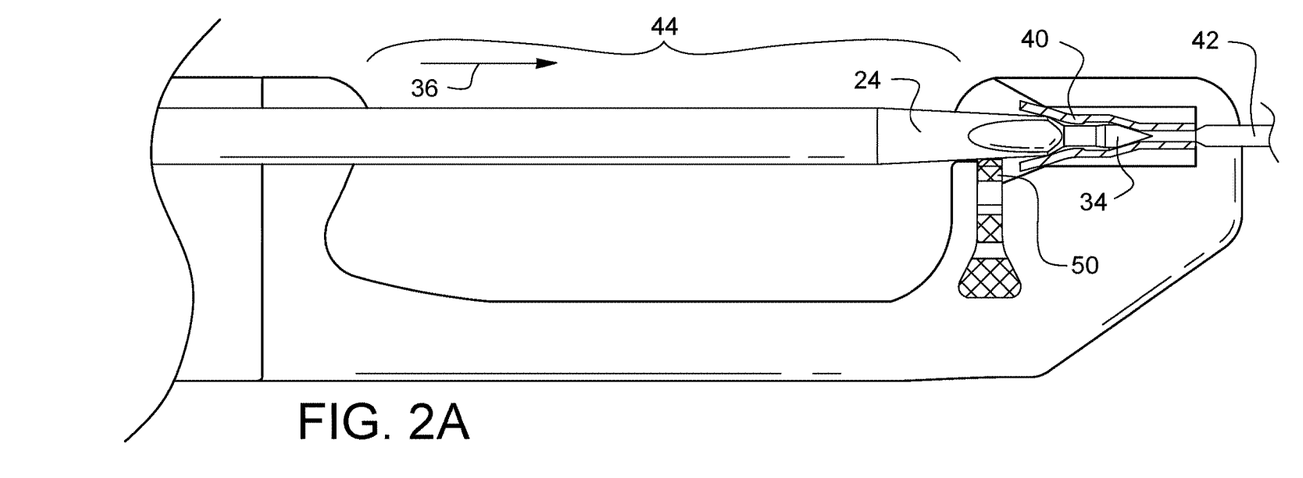
FIGS. 2A and 2B are enlarged views of the distal end of the device 20 from FIG. 1 illustrating what can happen if the needle tip is advanced too far.
Figure 2B:
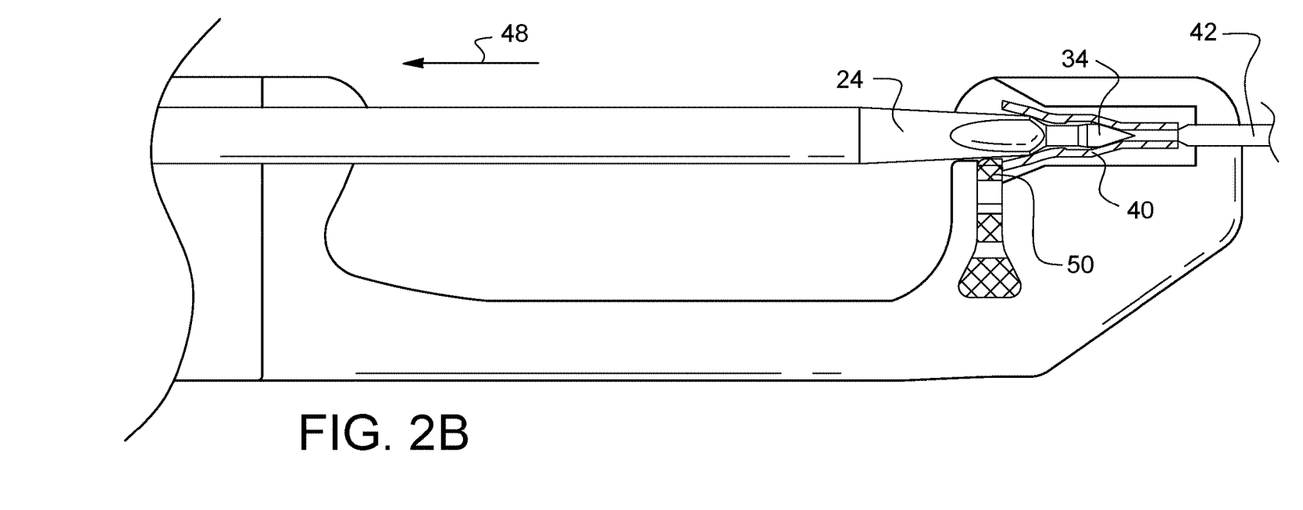
Figure 3A:
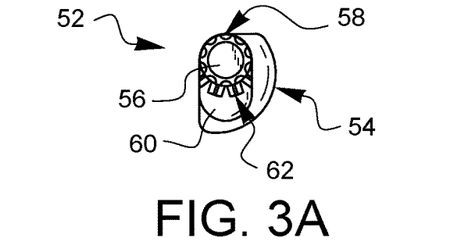
FIGS. 3B, 3C, 3D, 3A, 3E, and 3F are front, left, right, top, bottom, and upside-down back views, respectively, of one embodiment of an adjustable motion limiter for a minimally invasive surgical device.
Figure 3B:
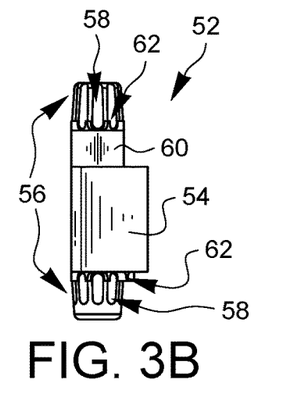
Figure 3C:
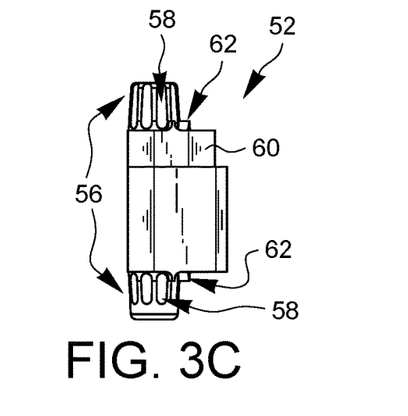
Figure 3D:
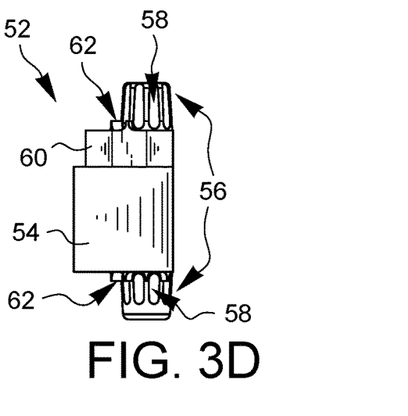
Figure 3E:
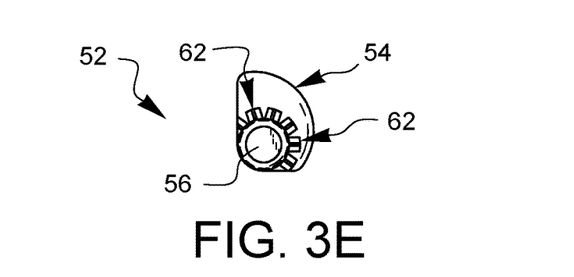
Figure 3F:
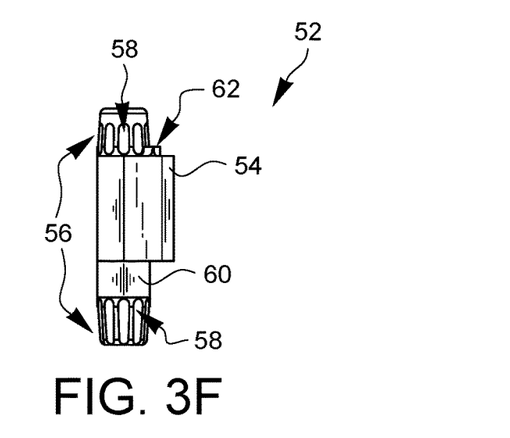

FIGS. 2A and 2B are enlarged views of the distal end of the device 20 from FIG. 1 illustrating what can happen if the needle tip 34 is advanced too far. In this case, as demonstrated in FIG. 2A, the interference of the needle tip 34 and the ferrule 40 causes the ferrule to flare out as the larger portion of the needle 24 is driven into contact with the ferrule 40. When the needle 24 tries to move back in a proximal direction 48, as shown in FIG. 2B, the flared ferrule 40 contacts a release spring 50 when it is not supposed to. Depending on how tightly the needle 24 is wedged into the ferrule 40, this can jam the device or cause the ferrule 40 to release from the needle 24 when such release is not desired. In either case, the device does not work properly. The tolerance stack can vary from unit to unit, so it would be advantageous to have a device and method to compensate for the effects of the tolerance stack, thereby ensuring reliable device operation.

SUMMARY

An adjustable motion limiter for a minimally invasive surgical device is disclosed. The adjustable motion limiter includes a cam surface and a positioning interface.

Another adjustable motion limiter for a minimally invasive surgical device is disclosed. The adjustable motion limiter has a positioning interface comprising a grooved protrusion. The adjustable motion limiter also has a cam surface comprising an arcuate surface and facing a direction which is substantially perpendicular to a direction the positioning interface faces. The adjustable motion limiter further has an adjustment key and one or more locking teeth.

A minimally invasive surgical device is also disclosed. The minimally invasive surgical device has an end effector. The minimally invasive surgical device also has an actuator coupled to the end effector. The minimally invasive surgical device further has an adjustable motion limiter. The adjustable motion limiter has a cam surface configured to engage the actuator. The adjustable motion limiter also has a housing interface.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIGS. 3B, 3C, 3D, 3A, 3E, and 3F are front, left, right, top, bottom, and upside-down back views of one embodiment of an adjustable motion limiter 52 for a minimally invasive surgical device. For convenience, the surgical device illustrated herein is a surgical suturing device, but other types of minimally invasive surgical devices could benefit from the claimed invention, including, but not limited to mechanical fastener applicators.

The adjustable motion limiter has a cam surface 54 and a positioning interface 56. In this embodiment, the cam surface 54 is a varying arcuate surface. Other embodiments may have other types of varying surfaces, including those which are continuously varying or discretely varying. The positioning interface 56 in this embodiment protrudes in two opposite directions which are each substantially perpendicular to a direction which the cam surface 54 faces. While this embodiment has a positioning interface 56 which features two protrusions, other embodiments may have a positioning interface which has fewer or more protrusions. Still other embodiments may have positioning interfaces which are holes or depressions or a mixture of holes and protrusions. As will be seen in further figures, in this embodiment, the adjustable motion limiter 52 is configured so that the cam surface 54 will engage an actuator, while the positioning interface 56 is configured to engage a housing. In other embodiments, the cam surface may be configured to engage a housing, while the positioning interface engages an actuator.

In this embodiment, the positioning interface 56 is grooved 58 to help keep the motion limiter 52 from rotating once it is pressed into the portion of the handle which it engages. In this embodiment, the positioning interface 56 is also tapered to facilitate the pressing of the interface 56 into a portion of the handle by easing the adjustable motion limiter 52 into place.

This embodiment of a motion limiter 52 also has an adjustment key 60 which happens to be an oblong rounded shape. Other embodiments may have other keyed shapes. A tool may be provided which can engage the adjustment key 60 in order to enable an assembler or an assembly machine to rotate the adjustable motion limiter 52. While the positioning interface 56 may be capable of holding the adjustable motion limiter 52 in place on its own, some embodiments, such as the one illustrated in FIGS. 3A-3F may include one or more locking teeth 62 which can help grip the material which the positioning interface 56 is pressed into.

Figure 4A:
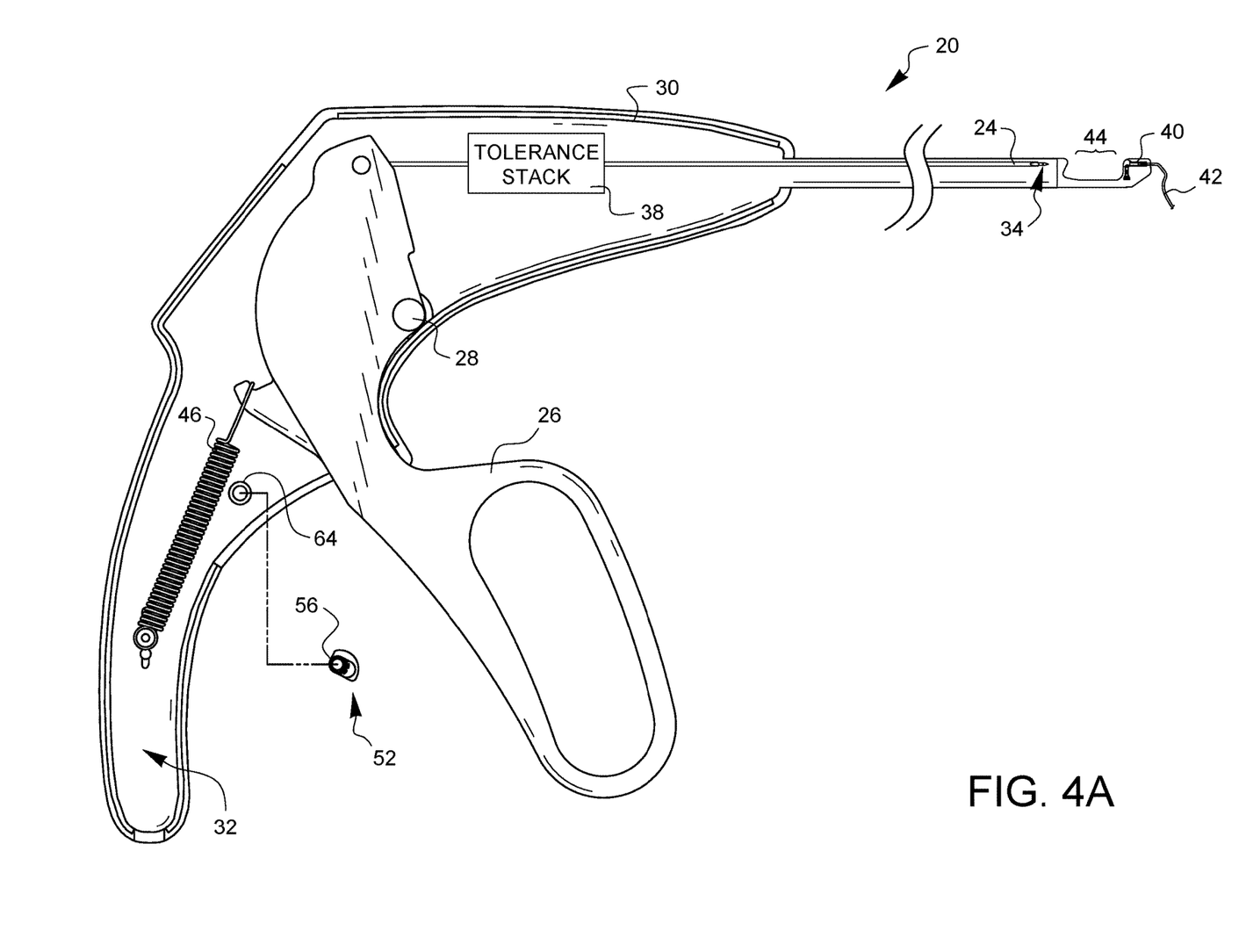
FIGS. 4A and 4B illustrate the adjustable motion limiter of FIGS. 3A-3F along with a schematic view of a minimally invasive surgical device in both a side and a perspective view, respectively.
Figure 4B:
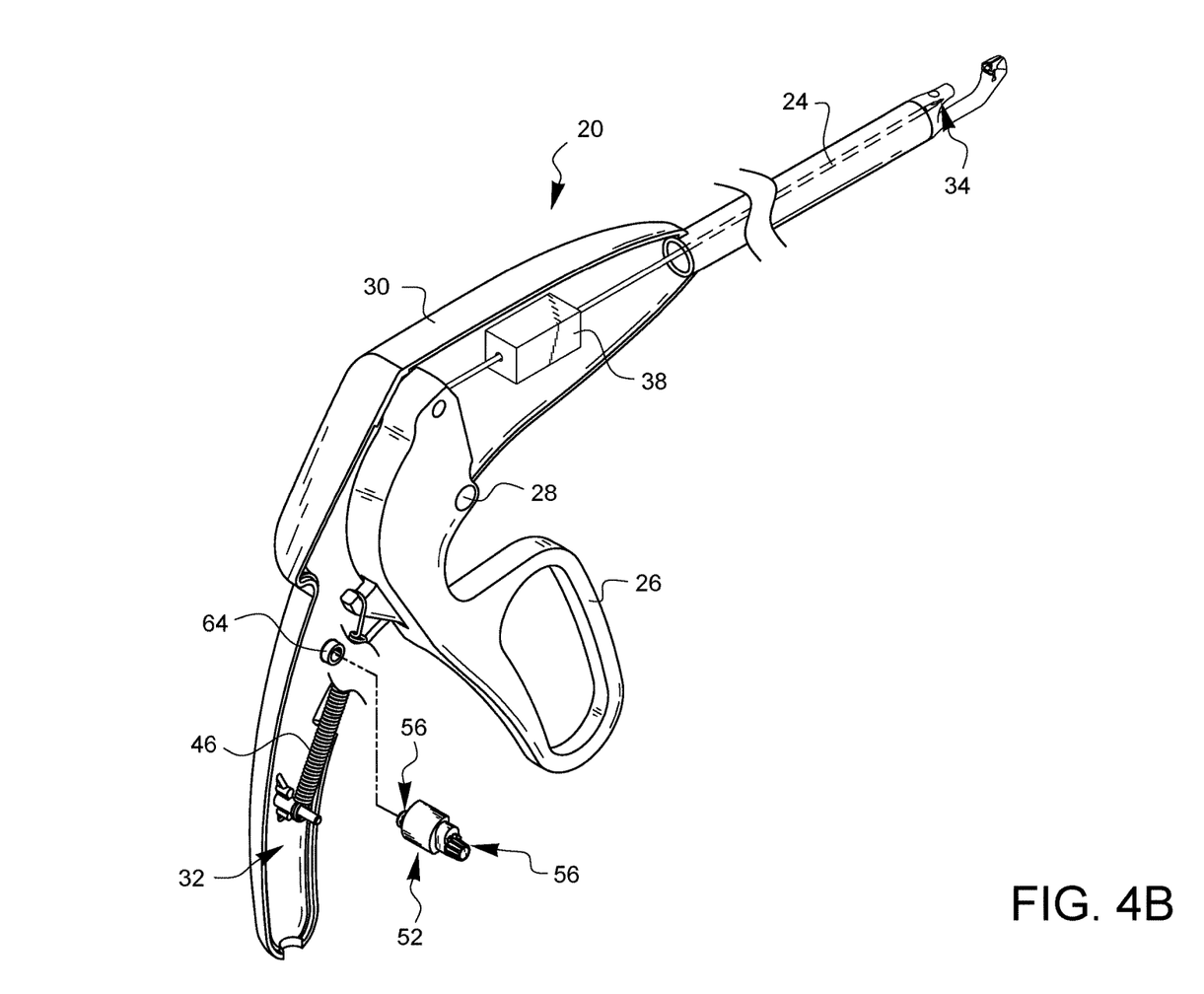

FIGS. 4A and 4B illustrate the adjustable motion limiter 52 of FIGS. 3A-3F along with a schematic view of a minimally invasive surgical device 20 in both a side and a perspective view, respectively. The adjustable motion limiter 52 is exploded away from the device housing/handle 30/32 in order to show a boss 64 which has been formed in the housing 30 in order to receive the positioning interface 56. Only one half of the handle 32 is illustrated here for convenience, but it should be understood that a corresponding boss may be provided on the other handle half if the positioning interface 56 also extends in that direction.

Figure 5:
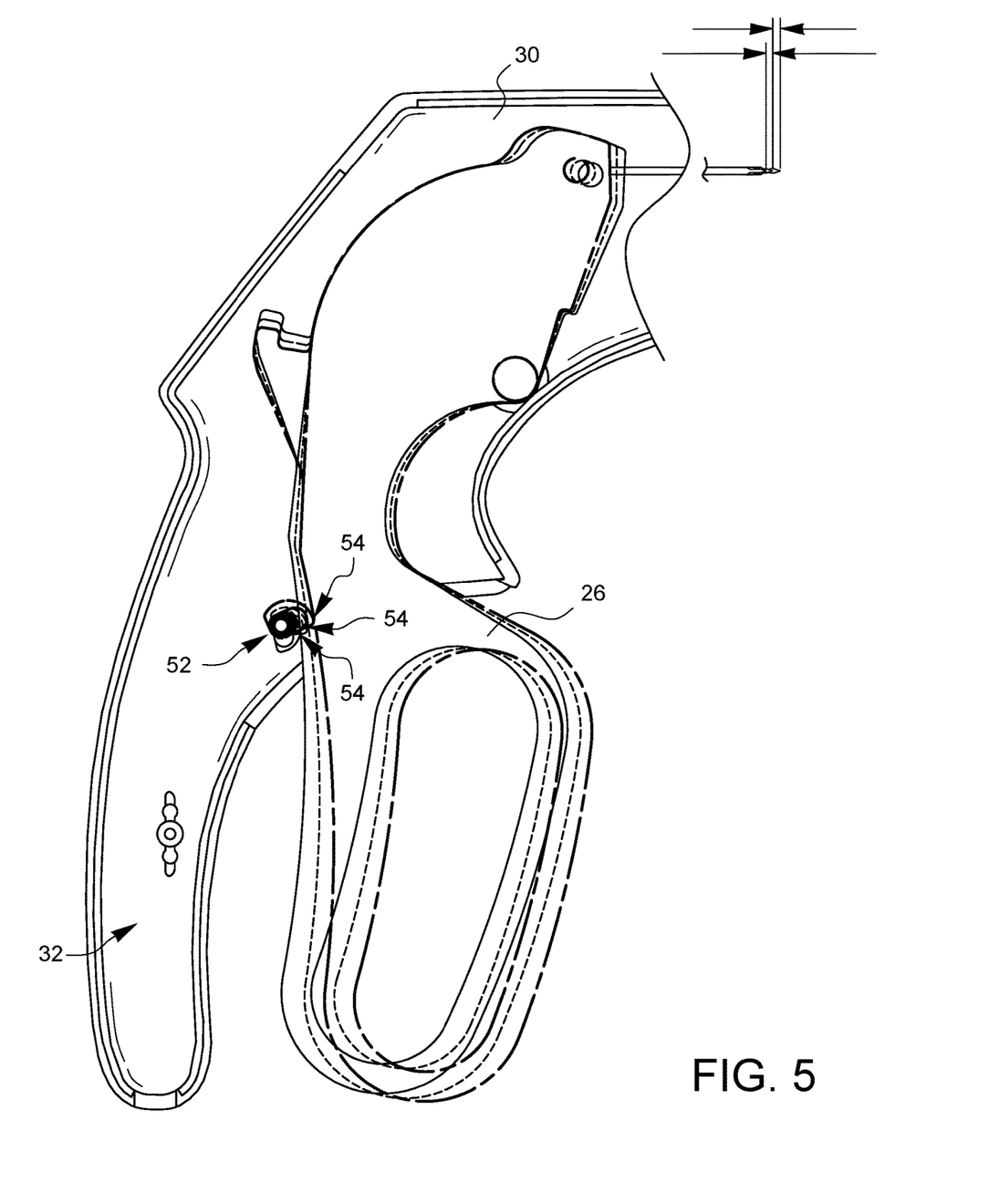
FIG. 5 illustrates three possible positions for the cam surface of the adjustable motion limiter of FIGS. 3A-3F and the corresponding farthest travel possible for an actuator of a surgical device, depending on the position of the cam surface.

As illustrated in FIG. 5, the adjustable motion limiter 52 may be rotated before being pressed into the boss 64 to position the cam surface 54 at different profiles relative to the actuator 26. Three potential profiles out of numerous profiles are shown in FIG. 5 to illustrate the benefit of the adjustable motion limiter 52. The first profile is illustrated as a thinner solid line. In this first position, the cam surface 54 does not reach out towards the actuator 26 as far as the other illustrated positions. Accordingly, the actuator may be moved back towards the handle 32 farther than when the other profiles are used before the actuator 26 contacts the cam surface 54 of the adjustable motion limiter 52. This profile position would allow the needle tip 34 to travel farther when the actuator is engaged fully.

By contrast, the second profile is illustrated as a thicker, occasionally broken line. In this second position, the cam surface 54 reaches out farther towards the actuator 26 than the other illustrated positions. Accordingly, the actuator may be moved back towards the handle 32 less than when the other profiles are sued before the actuator 26 contacts the cam surface 54 of the adjustable motion limiter 52. This profile position would allow the needle tip 34 to travel less when the actuator is fully engaged.

As a further example, the third profile is illustrated as a thin, regularly broken line. This third position is located between the first and second positions, and as such, the actuator may be moved a distance between those possible in the first and second positions before the actuator contacts the cam surface 54 of the adjustable motion limiter 52. This profile position would allow the needle tip 34 to travel a distance between those possible with the first and second positions when the actuator is fully engaged.

An operator or automated assembly fixture may be used to rotate the adjustable motion limiter 52 while the actuator is fully engaged to a desired amount of travel. The desired amount of travel can be determined by looking at the position of the needle tip 34 relative to the device tip, a ferrule holder of the device, or even a ferrule installed in the device. The adjustable motion limiter 52 should be rotated until the cam surface contacts the actuator 26 in this desired full-travel position, and then the adjustable motion limiter 52 can be fixed in place by one or more methods which include, but are not limited to pressing, welding, and gluing the limiter to the housing 30.

Figure 6:
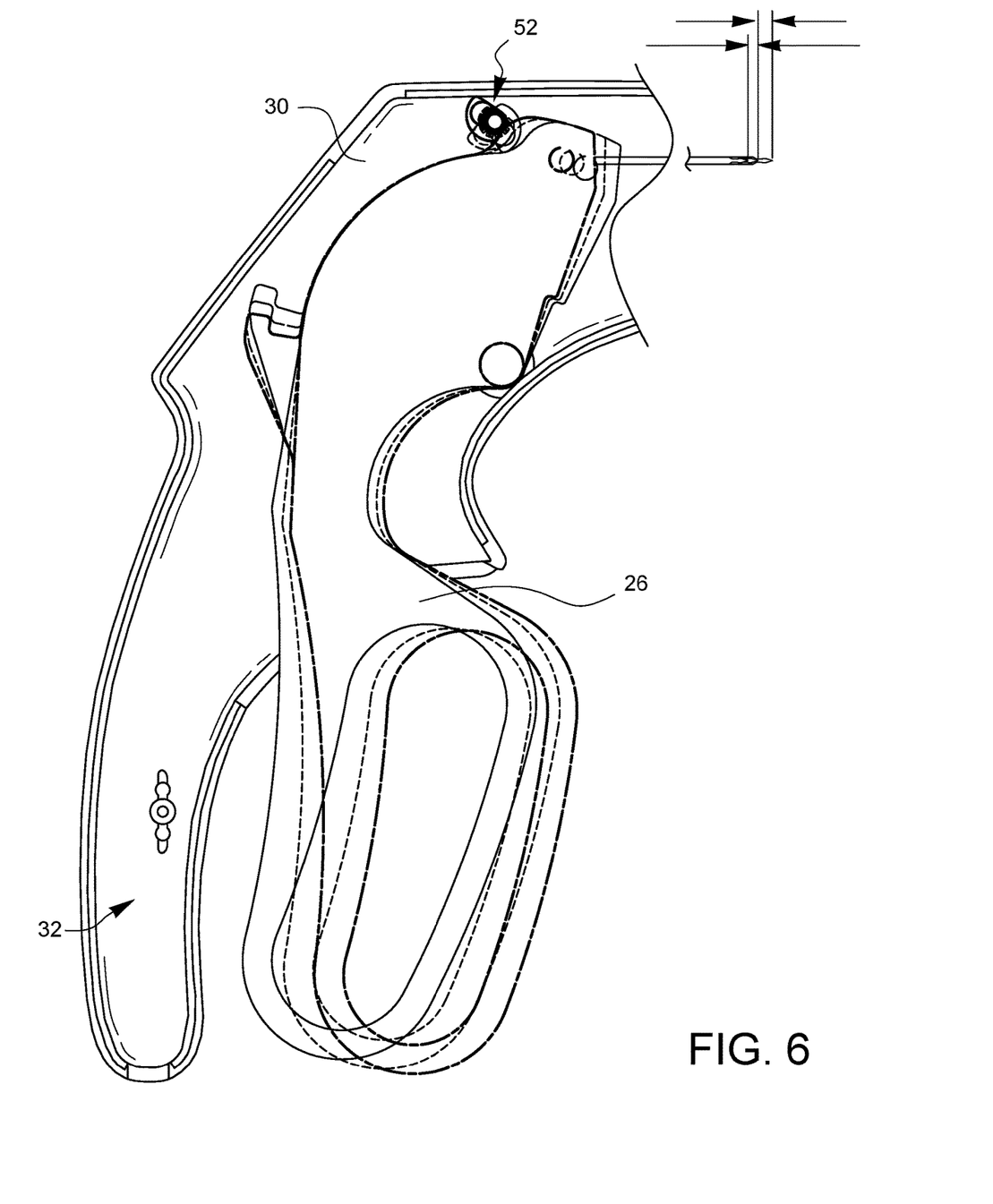
FIG. 6 is similar to FIG. 5, however the location of the adjustable motion limiter has been modified.

FIG. 6 illustrates another potential position on the housing where the motion limiter 52 could be fixed to the housing 30. As mentioned earlier, in other embodiments, the motion limiter 52 could be fixed to the actuator in a place where it would contact a known part of the housing.

Figure 7:
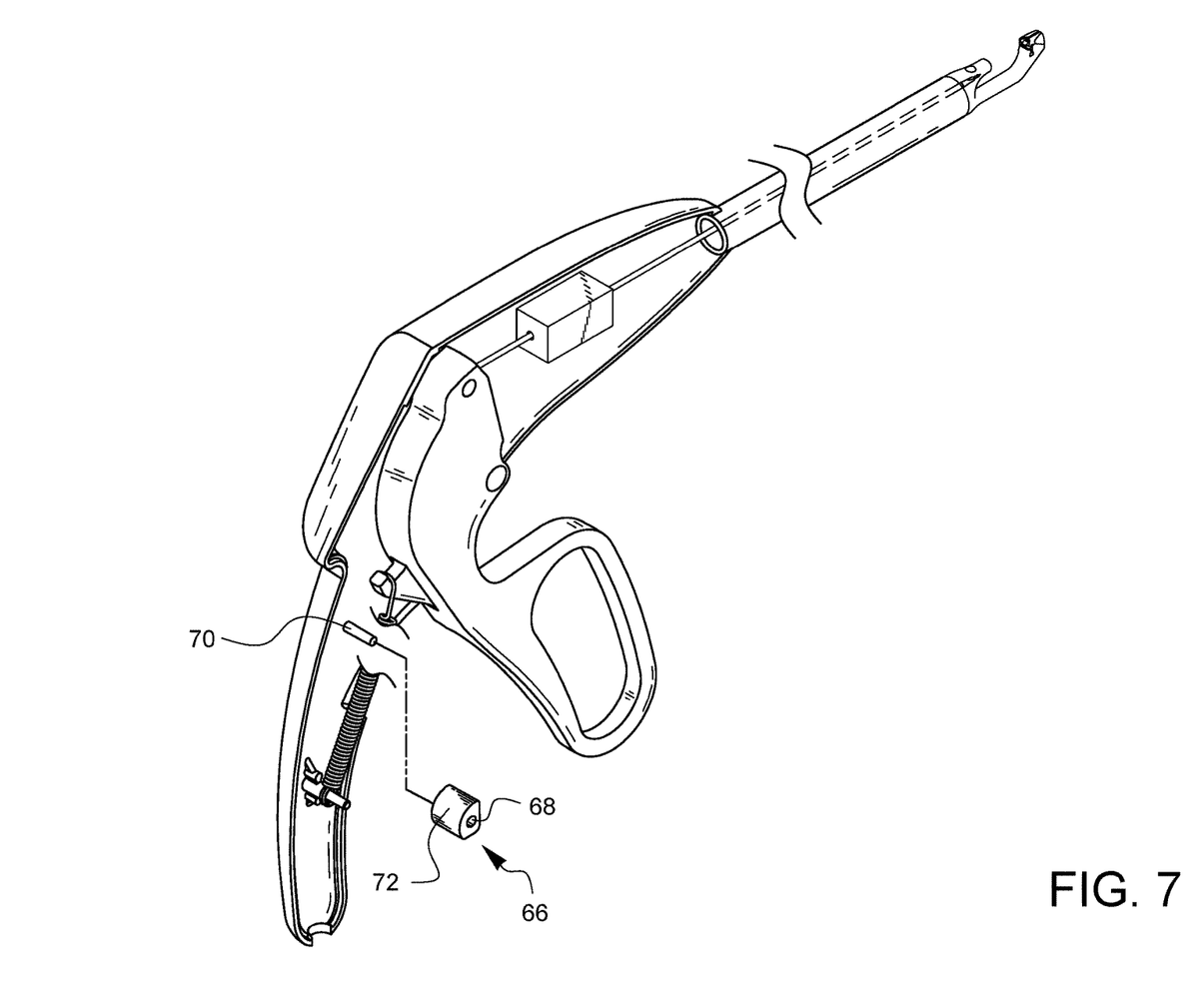
FIG. 7 illustrates another embodiment of an adjustable motion limiter.

FIG. 7 illustrates another embodiment of an adjustable motion limiter 66, this one having holes 68 for its positioning interface. In this embodiment, a corresponding protrusion 70 is provided on the handle. Adjustment of the cam surface 72 of the motion limiter 66 would occur similarly to the examples described above.

Figure 8A:
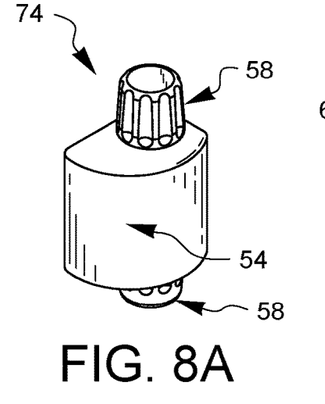
FIGS. 8A-8E are each further embodiments of an adjustable motion limiter.
Figure 8B:
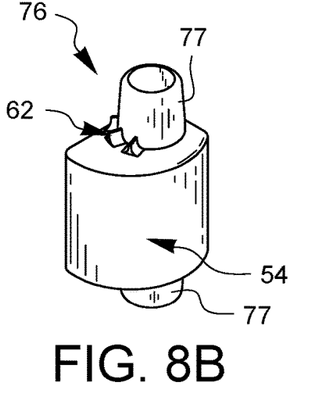
Figure 8C:
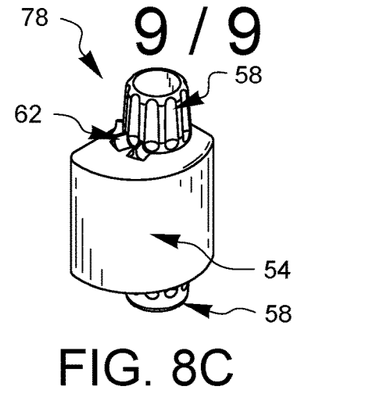
Figure 8D:
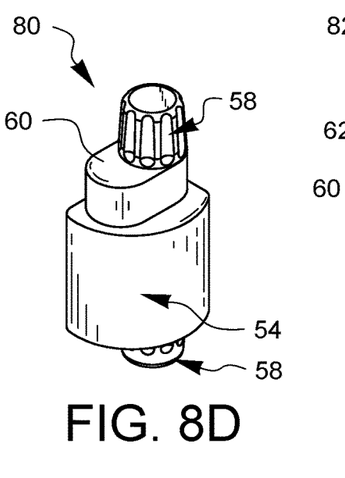
Figures 8E, 8F:
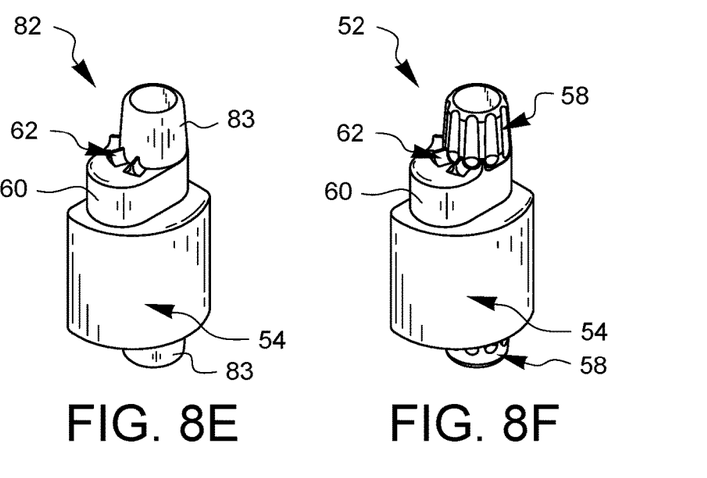
FIG. 8F is an enlarged perspective view of the adjustable motion limiter of FIGS. 3A-3F.
Figure 8G:
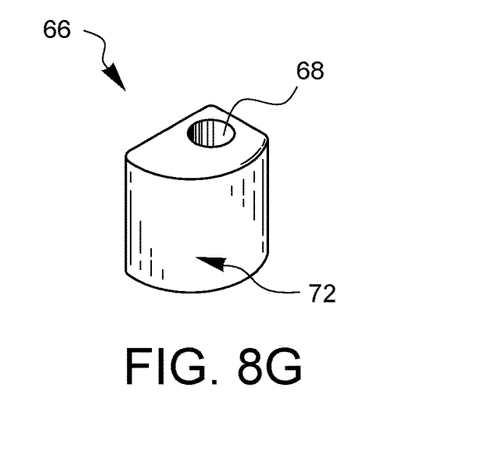
FIG. 8G is an enlarged perspective view of the adjustable motion limiter of FIG. 7.

FIGS. 8A-8G illustrate different non-limiting embodiments of an adjustable motion limiter. The adjustable motion limiter 74 of FIG. 8A is like that of FIGS. 3A-3F, except the motion limiter 74 does not have an adjustment key or locking teeth. The adjustable motion limiter 76 of FIG. 8B is like that of FIGS. 3A-3F, except the motion limiter 76 does not have an adjustment key or grooved protrusions. Instead, the protrusions 77 which make up the positioning interface are smooth. Locking teeth, however, are provided. The adjustable motion limiter 78 of FIG. 8C is like that of FIGS. 3A-3F, except the motion limiter 78 does not have an adjustment key. The adjustable motion limiter 80 of FIG. 8D is like that of FIGS. 3A-3F, except the motion limiter 80 does not have locking teeth. The adjustable motion limiter 82 of FIG. 8E is like that of FIGS. 3A-3F, except the motion limiter 82 does not have grooved protrusions. Instead, the protrusions 83 which make up the positioning interface are smooth. The adjustable motion limiter 52 of FIG. 8F is like that of FIGS. 3A-3F. The adjustable motion limiter 66 of FIG. 8G is like that of FIG. 7.

Various advantages of an adjustable motion limiter for a minimally invasive surgical device have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An adjustable motion limiter for a minimally invasive surgical device, the adjustable motion limiter comprising:
   a cam surface configured to contact an actuator coupled to the minimally invasive surgical device; and
   a positioning interface which is fixed in place and protrudes in a fixed direction relative to the cam surface and facing a direction substantially perpendicular to a direction which the cam surface faces.

2. The adjustable motion limiter of claim 1, wherein the cam surface comprises an arcuate surface.

3. The adjustable motion limiter of claim 1, wherein the cam surface comprises a varying arcuate surface.

4. The adjustable motion limiter of claim 1, wherein the cam surface comprises a continuously varying arcuate surface.

5. The adjustable motion limiter of claim 1, wherein the cam surface comprises multiple discrete arcuate surfaces.

6. The adjustable motion limiter of claim 1, wherein the positioning interface comprises a tapered protrusion.

7. The adjustable motion limiter of claim 1, wherein the positioning interface comprises a grooved protrusion.

8. The adjustable motion limiter of claim 1, wherein the positioning interface comprises a hole.

9. The adjustable motion limiter of claim 1, wherein the positioning interface comprises multiple protrusions.

10. The adjustable motion limiter of claim 1, further comprising an adjustment key.

11. The adjustable motion limiter of claim 1, further comprising one or more locking teeth.

12. The adjustable motion limiter of claim 1, wherein the positioning interface is configured to engage a housing.

13. An adjustable motion limiter for a minimally invasive surgical device, the adjustable motion limiter comprising:
   a positioning interface comprising a grooved protrusion which is fixed in place;
   a cam surface configured to engage an actuator of the minimally invasive surgical device, the cam surface comprising an arcuate surface and facing a fixed direction relative to the positioning interface and facing a direction which is substantially perpendicular to a direction the positioning interface faces;
   an adjustment key; and
   one or more locking teeth.

14. A minimally invasive surgical device comprising:
   an end effector;
   an actuator coupled to the end effector; and
   an adjustable motion limiter comprising:
      a cam surface configured to engage the actuator; and
      a housing interface which is fixed in place and faces in a fixed direction relative to the cam surface and facing a direction substantially perpendicular to a direction which the cam surface faces.

15. The minimally invasive surgical device of claim 14, wherein the end effector comprises a needle.

16. The minimally invasive surgical device of claim 14, wherein the end effector comprises a crimper for a mechanical knotting device.

17. The minimally invasive surgical device of claim 14, wherein the actuator comprises a lever.

18. The minimally invasive surgical device of claim 14, wherein the adjustable motion limiter is inaccessible to an operator of the minimally invasive surgical device.

* * * * *